US007662781B2

(12) United States Patent
Kanegasaki et al.

(10) Patent No.: US 7,662,781 B2
(45) Date of Patent: Feb. 16, 2010

(54) IMMUNOPOTENTIATING AGENT (75) Inventors: Shiro Kanegasaki, Tokyo (JP); Takuya Tamatani, Kanagawa (JP)

(73) Assignee: ECI, Inc., Tokyo (JP)

(*) Notice: Subject to any disclaimer, the term of this patent is extended or adjusted under 35 U.S.C. 154(b) by 231 days.

(21) Appl. No.: 11/883,302

(22) PCT Filed: Dec. 20, 2005

(86) PCT No.: PCT/JP2005/023844

§ 371 (c)(1),
(2), (4) Date: Jul. 30, 2007

(87) PCT Pub. No.: WO2006/080171

PCT Pub. Date: Aug. 3, 2006

(65) Prior Publication Data
US 2009/0054318 A1 Feb. 26, 2009

(30) Foreign Application Priority Data
Jan. 31, 2005 (JP) ............................. 2005-023224
Sep. 14, 2005 (JP) ............................. 2005-266381

(51) Int. Cl.
A61K 38/00 (2006.01)
C07K 5/00 (2006.01)
(52) U.S. Cl. ........................................ 514/12; 530/324
(58) Field of Classification Search .................. None
See application file for complete search history.

(56) References Cited

U.S. PATENT DOCUMENTS

| 4,705,955 | A | * | 11/1987 | Mileikowsky ............ 250/492.1 |
|---|---|---|---|---|
| 4,847,325 | A | | 7/1989 | Shadle et al. |
| 5,616,688 | A | | 4/1997 | Cerami et al. |
| 5,824,784 | A | | 10/1998 | Kinstler et al. |
| 5,922,597 | A | | 7/1999 | Verfaillie et al. |
| 5,925,568 | A | | 7/1999 | Comer et al. |
| 5,977,310 | A | | 11/1999 | Namiki et al. |
| 5,985,265 | A | | 11/1999 | Kinstler et al. |
| 6,046,309 | A | | 4/2000 | Cerami et al. |
| 6,057,123 | A | | 5/2000 | Craig et al. |
| 2006/0210531 | A1 | | 9/2006 | Matsushima et al. |
| 2008/0124307 | A1 | | 5/2008 | Matsushima et al. |

FOREIGN PATENT DOCUMENTS

| AU | 741472 B2 | 3/1999 |
|---|---|---|
| CA | 2 036 197 C | 9/2001 |
| EP | 0 136 792 A3 | 4/1985 |
| EP | 0 154 316 A2 | 9/1985 |
| EP | 0 210 761 A1 | 2/1987 |
| EP | 0 442 724 A2 | 8/1991 |
| EP | 0 510 356 A1 | 10/1992 |
| EP | 0 898 968 A1 | 3/1999 |
| EP | 1 013 276 A1 | 6/2000 |
| EP | 0 923 566 B1 | 10/2003 |
| EP | 0 816 381 B1 | 1/2004 |
| EP | 1 563 847 A1 | 8/2005 |
| JP | 61-178926 A | 8/1986 |
| JP | 62-115280 A | 5/1987 |
| JP | 5-117300 A | 5/1993 |
| JP | 6-256394 A | 9/1994 |
| JP | 8-511263 A | 11/1996 |
| JP | 9-25298 A | 1/1997 |
| JP | 10-513187 A | 12/1998 |
| JP | 11-60499 A | 3/1999 |
| JP | 11-310600 A | 11/1999 |
| JP | 2000-157285 A | 6/2000 |
| JP | 2000-517304 A | 12/2000 |
| JP | 2004-194770 A | 7/2004 |
| JP | 2004-196770 A | 7/2004 |
| WO | WO-96/23794 A1 | 8/1996 |
| WO | WO-96/28475 A1 | 9/1996 |
| WO | WO-99/11666 A1 | 3/1999 |
| WO | WO-00/47228 A1 | 8/2000 |
| WO | WO-01/54727 A1 | 8/2001 |
| WO | WO-01/83548 A1 | 11/2001 |
| WO | WO-2004/024088 A2 | 3/2004 |

OTHER PUBLICATIONS

Burgess et al, Journal of Cell Biology vol. 111 Nov. 1990 2129-2138.*
Lazar et al Molecular and Celular Biology vol. 8 p. 1247 (1988).*
Taruki et al., "Mobilization of Dendritic Cells Into Solid Tumour by Administration of Styrene-maleic acid (SMA) Copolymer Conjugated MIP-1alpha (SMIP) in Mice," Seikagaku, vol. 76, No. 8, 2004, pp. 986.
Menten et al., "Macrophage inflammatory protein-1," Cytokine Growth Factor Rev., vol. 13, 2002, pp. 455-481.
Horiuchi et al., "Abscopal effect o Mitometa Shocho NK/T Saibo Lymphoma," Rinsho Ketsueki, vol. 44, No. 9, 2003, pp. 940-945.
Demaria et al., "Ionizing Radiation Inhibition of Distant Untreated Tumors (Abscopal Effect) is Immune Mediated," Int. J. Radiat. Oncol. Biol. Phys., vol. 58, No. 3, 2004, pp. 862-870.
Gazzaniga et al., "Inflammatory Changes after Cryosurgery-Induced Necrosis in Human Melanoma Xenografted in Nude Mice," J. Invest. Dermatol., vol. 116, No. 5, 2001, pp. 664-671.
Wu et al., "Activated Anti-tumor Immunity in Cancer Patients after High Intensity Focused Ultrasound Ablation," Ultrasound in Med. & Biol., vol. 30, No. 9, 2004, pp. 1217-1222.

(Continued)

Primary Examiner—Sheela J Huff
(74) Attorney, Agent, or Firm—Birch, Stewart, Kolach & Birch, LLP (57) ABSTRACT Satisfactory effects have not always been attained by immunotherapy having been tried, and reliance upon direct attack on cells by anticancer agents, radiation, etc has been inevitable. The present invention intends to provide a therapeutic method that ensures less side effects but higher efficacy than in conventional therapeutic methods through enhancing of immune strength inherently had by living organism. Thus, the present invention relates to an immunopotentiating agent comprising MIP-1α or its functional derivative as an active ingredient.

34 Claims, 6 Drawing Sheets

OTHER PUBLICATIONS

English translation of the International Preliminary Report on Patentability dated Feb. 14, 2008, issued in connection with International Application No. PCT/JP2005/023884 filed Dec. 20, 2005.
Abuchowski et al., Cancer Biochem Biophys., vol. 7, pp. 175-186 (1984).
Yoshimoto et al. Jpn. J. Cancer Res. (Gann), vol. 77, pp. 1264-1270 (Dec. 1986).
Inaba et al., J Exp. Med., vol. 176, pp. 1693-1702 (Dec. 1992).
Hunter at al. Blood, vol. 86, No. 12, pp. 4400-4408 (Dec. 15 1995).
Fujioka et al., Journal of Leukocyte Biology, vol. 58, pp. 90-98 (Jul. 1995).
Bernstein et al., British Journal of Haematology, vol. 99, pp. 888-895 (1997).
Caux et al. Blood, vol. 90, No. 4, pp. 1458-1470 (Aug. 15 1997).
Zhang et al., Blood, vol. 90, No. 12, pp. 4842-4853 (Dec. 15, 1997).
Hart. Blood. vol. 90, No. 9, pp. 3245-3287 (Nov. 1, 1997).
Gao et al., The Journal of Experimental Medicine, vol. 185, No. 11, pp. 1959-1968 (Jun. 2, 1997).
Caux et al., Dendritic Cells in Fundamental and Clinical Immunology, vol. 3, Series: Adv. Exp. Med. Biol., vol. 417, pp. 21-25 (1997).
Marshall et al., European Journal of Cancer, vol. 34, No. 7, pp. 1023-1029 (1998).
Clemons at al., Blood, vol. 92, No. 5, pp.1532-1540 (Sep. 1, 1998).
Broxmeyer et al., Blood Cells, Molecules, and Diseases, vol. 24, No. 2, pp. 14-30 (Jan. 31, 1998).
Banchereau et al., Nature, vol. 392, pp. 245-252 (Mar. 19 1998).
Zhang et al, Blood, vol. 92, No. 1, pp. 118-128 (Jul. 1, 1998).
Dieu et al., J. Exp. Med., vol. 188, No. 2, pp. 373-386 (Jul. 20, 1998).
Zhang et al., Blood, vol. 93, No. 4, pp.1208-1220 (Feb. 15, 1999).
Ogata et al., Blood, vol. 93, No. 10, pp. 3225-3232 (May 15, 1999).
Zhang et al., Blood, vol. 95, No. 1, pp. 138-146 (Jan. 1, 2000).
Klein et al., J. Exp. Med., vol. 191, No. 10. pp. 1699-1708 (May 15, 2000).
Sallusto et al., Immunological Reviews, vol. 177, pp. 134-140 (2000).
Ali et al., The Journal of Biological Chemistry, vol. 275, No, 16, pp. 11721-11727 (Apr. 21, 2000).
Sozzani et al., Journal of Clinical Immunology, vol. 20, No. 3, pp. 151-160 (2000).
Allavena et al., Immunological Reviews, vol. 177, pp. 141-149 (2000).
Inaba, Cell Technology, vol. 19, No. 9, pp. 1282-1286 (2000).
Kawamoto et al., Cell Technology, vol. 19, No. 9, pp. 1289-1293 (2000).
Iyoda et al., Cell Technology, vol. 19 No. 9. pp. 1311-1317 2000.
Nakano, Cell Technology, vol. 19 No. 9, pp. 1304-1310 (2000).
Chemokine Handbook, front page, pp. 68-70, 84-86, 87-90, and publication data, Edited by O. Yosie et al., (Nov. 20, 2000).
Lin et al, J. Exp. Med., vol. 192, No. 4, pp. 587-593 (Aug. 21, 2000).
Takayama et al., Molecular Cell Therapy, vol. 2, No, 6, p. 53-56 (2001).
Yoneyama et al., J. Exp. Med., vol, 193. No. 1, pp. 35-49 (Jan. 1. 2001).
Uwatoku et al., Gastroenterology, vol. 121, pp. 1460-1472 (2001).
Zoffmann et al, J. Med. Chem., vol. 44, pp. 215-222 (2001).
Nomiyama et al., International Immunology, vol. 13, No. 8, pp. 1021-1029 (Mar. 1, 2001).
Weber et al., Blood, vol. 97, No. 4, pp. 1144-1146 (Feb. 15, 2001).
Dong et al., Biochemical and Biophysical Research Communications, vol. 298 pp. 675-686 (2002).
Yoneyama et al., J. Exp. Med., vol. 195, No. 10, pp. 1257-1266 (May 20, 2002).
Steinman et al., The Journal of Clinical Investigation, vol. 109, No. 12, pp. 1519-1526 (Jun. 2002).
Gillet et al J. Exp. Med., vol. 195, No. 7, pp. 953-958 (Apr. 1, 2002).
del Hoyo et al., Nature, vol. 415, pp. 1043-1047 (Feb. 28, 2002).
Matsuno, Progress of Medicine, vol. 200, No. 6 pp. 132-136 (2002).
Kuraoka et al., International Journal of Oncology, vol. 23, pp. 421-427 (2003).
O'Keeffe et al., Blood, vol. 101, No. 4, pp. 1453-1459 (Feb. 15, 2003).
Murai et al., Nature Immunology, vol. 4, No. 2, pp. 154-160 and 497 (Feb. 2003).
Zhang et al., Journal of the National Cancer Institute, vol. 96, No. 3, pp. 201-209 (Feb. 4, 2004).
McKay et al., Eur. J. Immunol., vol. 34, pp. 1011-1020 (2004).
Kaminski et al., Cancer Treatment Reviews, vol. 31, pp. 159-172 (2005).
Azuma et al., "Trial of Enhancing Anti-Tumor Immunity with Immunological Adjuvant", vol. 9, Supplement. I, Feb. 1982, 40th Annual Meeting of the Japanese Cancer Association, Special Issue.
Nakano et al., "Induction of Dendritic Cell Precursors by MIP-1a and the Test of Their Effect on Tumor Regression", Proceedings of the Japanese Society for Immunology, 2004, vol. 34, pp. 214.
Tanio et al., "Comparison of Antimetastatic Effect Against Lewis Lung Carcinoma After Intratumoral and Intravenous Injections of Cell-Wall Skeleton of Propionibacterium Acnes C7 in C57B/J6 Mice", Gann, vol. 75, Mar. 1984, pp. 237-244.

* cited by examiner

IMMUNOPOTENTIATING AGENT

TECHNICAL FIELD

The present invention relates to an immunopotentiating agent which is useful in, for examples, treating cancer, inhibiting cancer metastasis and treating an immunologic disease such as pollinosis.

BACKGROUND OF THE ART

Although a large number of cancer cells develop everyday in vivo, these cancer cells are eliminated in many cases owing to the system for eliminating abnormal cells and the immune system. This prediction that cancer cells are eliminated by the immune system is supported by the fact that the incidence of cancer increases with the depression of the immune function caused by aging, an immunological disease such as AIDS or the administration of an immunosuppressive agent. From this viewpoint, immunotherapy for eradicating cancer through immunopotentiation has attracted public attention in recent years. However, the currently available immunotherapeutic methods for cancer frequently fail to induce immunity against cancer and thus efficacious treatments cannot be conducted thereby.

It is known that dendritic cells play an important role in inducing the immunity against cancer. We have already found out that MIP-1α or its functional derivative is capable of topically accumulating dendritic cells at an inflammation site or a cancer site. We have further found out that MIP-1α or its functional derivative can mobilize dendritic cell precursors several ten-fold in the blood (Yoneyama H. et al., J. Exp. Med., Vol. 193 (1), pp. 35-49 (2001); and Zhang Y. et al., J. Natl. Cancer Inst., Vol. 96, pp. 201-209 (2004)). Also, it is reported that the topical MIP-1α expression at an immune site of an immune-induced mouse results in the accumulation of dendritic cells and an antigen-specific immunity is thus induced (McKay P F et al., Eur. J. Immunol., Vol. 34, pp. 1011-1020 (2004)).

To inhibit the proliferation and metastasis of cancer cells, radiation therapy has been utilized in combination with surgery, chemotherapy, hormonal therapy and so on. However, it is difficult to completely eliminate cancer cells and, moreover, there arise some side effects such as the suppression of the immune system, a loss of appetite, anemia, a decrease in leukocytes and a decrease in platelets. Although these side effects can be relieved by stereotactic irradiation with an electron beam whereby a cancer tissue is topically treated, cancer cells can be hardly eradicated thereby. Accordingly, it has been required to develop a technique for improving and potentiating the inflammation that have been introduced into a cancer tissue by the electron beam irradiation or the functions of T cells and dendritic cells specific to cancer cells.

It is well known that the phenomenon of cancer metastasis is the most important factor in determining the prognosis of a cancer patient. However, the mechanism of "metastasis" still remains unsolved and no efficacious therapeutic method therefor has been established so far. There have been found out several biological components directly or indirectly relating to cancer metastasis. Further, antibodies to these components are constructed and somewhat effects are established on animal models of cancer metastasis. However, these antibodies have never been applied to humans hitherto. Although the currently available chemotherapeutics are efficacious against solid tumors, many of them exert only less effect on cancer metastasis than on cancer. Moreover, there is a problem that the development of drugs inhibiting the metastasis of cancer cells has made little progress. Under these circumstances, it has been urgently required to develop a drug which effectively inhibits the metastasis of cancer cells and improves the prognosis of a patient.

MIP-1α (Macrophage Inflammatory Protein-1α) is a molecule consisting of about 70 amino acids and belonging to the C—C chemokine family. It is released by activated lymphocytes, monocytes, etc. and induces the migration of dendritic cells, monocytes, Th1 cells and so on. MIP-1α is known as a ligand for CCR1 and CCR5 which are chemokine receptors expressed in immature dendritic cells (see, for example, Hideki Nakano, Saibo Kogaku, Vo. 19, No. 9, pp. 1304-1310 (2000)).

Also, there have been known functional derivatives of MIP-1α that are equivalent to biological activity of MIP-1α. In the case of MIP-1α, for example, a MIP-1α variant (hereinafter called eMIP or BB10010) in which Asp at the 26-position in MIP-1α is substituted by Ala and which is composed of 69 amino acids starting with Ser at the amino end is known. It is found out that this MIP-1α variant has a remarkably improved anticoagulant ability with an activity comparable to the wild type. And this variant has been investigated on improving leukopenia, which occurs as a side effect of chemotherapy for cancer (E. Marshall et al., European Journal of Cancer, Vol. 34, No. 7, pp. 1023-1029 (1998)).

It has been already known that neocarzinostatin chemically modified with a partially butyl-esterified styrene-maleic acid copolymer, which is an amphiphilic polymer, is usable as a carcinostatic agent (general name: zinostatin stimalamer) (Japanese Patent Publication of Examined Application No. 33119/1989). It is also known that, when administered into the blood, this drug accumulates almost selectively in a solid tumor and is sustained therein over a long period of time, i.e., showing the so-called EPR effect. Owing to these characteristics, it has been employed as a carcinostatic agent specifically targeting cancer. Also, a peptidic agonist chemically modified with an amphiphilic polymer and its functional derivative are known (WO 01/83548). Moreover, it is known that xanthine oxidase modified with polyethylene glycol shows the EPR effect on tumor cells (Japanese Patent Publication of Unexamined Application No. 060499/1999). In each of these cases, an antitumor effect is established by using a substance directly attacking against tumor cells. Namely, these methods aim at accumulating an aggressive substance selectively in a target site to thereby minimize the effects of the substance on normal cells or tissues.

It is also known that a protein modified with a polyethylene glycol derivative which is an amphiphilic polymer exhibits delayed clearance or lowered antigenicity in vivo (Yoshimoto et al., Jpn. J. Cancer Res., 77, 1264 (1986); Abuchowski et al., Cancer Biochem. Biophys., 7, 175 (1984); Japanese Patent Publication of Unexamined Application No. 178926/1986; Japanese Patent Publication of Unexamined Application No. 115820/1987; Domestic Re-publication of PCT international publication for patent application No. WO96/28475; Publication of Japanese translations of PCT international publication for patent application No. 513187/1999; Japanese Patent Publication of Unexamined Application No. 310600/1999, Publication of Japanese translations of PCT international publication for patent application No. 517304/2000). Furthermore, there are known interleukin-1, interleukin-6, interferon and so on each modified with polyethylene glycol (Japanese Patent Publication of Unexamined Application No. 117300/1993; Japanese Patent Publication of Unexamined Application No. 256394/1994; and Japanese Patent Publication of Unexamined Application No. 25298/1997).

DISCLOSURE OF THE INVENTION

As discussed above, these conventional immunotherapeutic methods cannot necessarily achieve satisfactory effects and, therefore, it is unavoidable to directly attack cancer cells with the use of, for example, a carcinostatic agent or radiation. An object of the present invention is to provide a therapeutic method of eliciting the immunity inherent to the living body to thereby exert an improved therapeutic effect yet showing less side effects compared with the currently available therapeutic methods.

Namely, the present inventors paid attention to the immunopotentiating effect of MIP-1α and its functional derivative such as eMIP, attempted to chemically modify them with the use of amphiphilic polymers, and consequently found out that the activity of such a chemically modified substance was not impaired but rather improved. Based on this finding, immunopotentiating agents comprising these substances as the active ingredient were invented.

Accordingly, the present invention relates to: (1) an immunopotentiating agent which comprises MIP-1α or its functional derivative as the active ingredient; (2) an immunopotentiating agent aiming at treating cancer by administering MIP-1α or its functional derivative in the state where inflammation has been induced; wherein (3) as the method of inducing inflammation, selection can be made of radiation irradiation, administration of an adjuvant, freezing and thawing the diseased part, ultrasonic irradiation or the like; and (4) a medicinal composition for immunotherapy which is a medicinal composition for immunotherapy comprising (a) a drug containing an adjuvant as the active ingredient and (b) a drug comprising MIP-1α or its functional derivative as the active ingredient, characterized in that the drugs (a) and (b) are simultaneously or sequentially administered.

The present invention further relates to: (5) an immunopotentiating agent which comprises MIP-1α or its functional derivative as an active ingredient for inhibiting cancer metastasis; or (6) an immunopotentiating agent which comprises MIP-1α or its functional derivative as an active ingredient for treating an immunologic disease; and (7) an immunopotentiating agent as described in the above (6) wherein the immunologic disease is pollinosis.

As the functional derivative of MIP-1α usable in the present invention, it is possible to select (8) eMIP or (9) MIP-1α or eMIP chemically modified with an amphiphilic polymer. As the amphiphilic polymer, use can be made of (10) a partially alkyl-esterified styrene/maleic acid copolymer or a polyethylene glycol derivative.

BEST MODE OF CARRYING OUT THE INVENTION

MIP-1α which is a typical example of the active ingredient in the present invention is known as a chemokine belonging to the CC subfamily. It is a ligand (an agonist) for receptors CCR1 and CCR5. It is considered that human matured MIP-1α is composed of 70 amino acids, while it is known that MIP-1α obtained from $CD8^+T$ cells or the culture supernatant of HTLV-1-infected cells MT4 has 66 amino acids. In human MIP-1α, there is a nonallelic gene LD78β having different copy numbers from individual to individual and one having a sequence different in three residues from the MIP-1α of 70 amino acid type is known. They are all usable in the present invention.

MIP-1α or its functional derivative usable in the present invention is a ligand or its derivative for a chemokine receptor CCR1 or CCR5 which has an effect as an agonist. That is, a functional derivative of MIP-1α means a derivative of MIP-1α which is comparable in biological activity as an agonist to MIP-1α. As a typical example of such biological equivalents, eMIP (ibid., European Journal of Cancer, Vol. 14, No. 7, pp. 1023-1029 (1998)) may be cited.

It has been confirmed that when MIP-1α or the like employed in the present invention as an immunopotentiating agent is chemically modified with an amphiphilic polymer typified by a partially alkyl-esterified styrene-maleic acid copolymer or a polyethylene glycol, it shows an improved stability in the blood while sustaining its activity. Thus, it is preferred to chemically modify MIP-1α or its functional derivative to be used in the present invention with an amphiphilic polymer. Such MIP-1α chemically modified with an amphiphilic polymer or a biological equivalent thereof is also referred to as "a functional derivative of MIP-1α" in the present description.

As preferable examples of the amphiphilic polymer to be used for chemically modifying MIP-1α or its biological equivalent in the present invention, partially alkyl-esterified styrene-maleic acid copolymers may be cited. As examples of the alkyl moiety thereof, linear or branched alkyl groups having from 1 to 5 carbon atoms may be cited. These alkyl groups may be substituted by a lower alkoxy group. More specifically speaking, examples thereof include methyl, ethyl, propyl, isopropyl, n-butyl, isobutyl, s-butyl, t-butyl, n-pentyl, 3-methyl-1-butyl, 2-methyl-1-butyl, 2,3-dimethyl-1-propyl, 2-pentyl, 3-methyl-2-butyl, 3-pentyl, 2-methyl-2-butyl, methylcellosolve, ethylcellosolve and so on.

A preferable example of the partially alkyl-esterified styrene-maleic acid copolymer is a partially butyl-esterified styrene-maleic acid copolymer having an average molecular weight of form 1,000 to 10,000 and a degree of polymerization of from 1 to 100, preferably form 3 to 35, as described in Japanese Patent Publication of Examined Application 1-33119.

Other examples of the amphiphilic polymer to be used for chemically modifying MIP-1α or its biological equivalent in the present invention, polyethylene glycol (hereinafter sometimes called PEG) derivatives may be cited. The term "polyethylene glycol derivative" as used herein means a compound having a residue capable of binding to a peptide chain in an agonist or its biological equivalent in the PEG moiety represented by —O—$(CH_2CH_2O)_n$— (wherein n is an integer of from 20 to 280). Examples of the polyethylene glycol derivatives include those having a residue capable of binding to an amino group (an N-terminal amino group or an amino group in a lysine residue) in a peptide chain. Other examples of the polyethylene glycol derivatives include those having a residue capable of binding to a carboxyl group (a C-terminal carboxyl group or a carboxyl group in an aspartic acid residue or a glutamic acid residue).

Still other examples of the amphiphilic polymers to be used in the present invention include polyvinylpyrrolidone and the like.

The chemically modified MIP-1α or a biological equivalent thereof according to the present invention can be obtained by chemically conjugating the amphiphilic polymer to MIP-1α or its biological equivalent optionally via a linker arm and then partially purifying. Namely, the amphiphilic polymer is reacted with MIP-1α or its biological equivalent in a buffer solution. Then the reaction product is purified by column chromatography and fractions thus eluted are separated.

Now, this process will be described in greater detail by taking the case wherein the amphiphilic polymer is a partially alkyl-esterified styrene-maleic acid copolymer for example. First, an acid anhydride of a styrene-maleic acid copolymer (SMA) obtained by radical copolymerization of styrene with maleic anhydride is dissolved in an organic solvent such as cumene. Then n-butanol is dropped into the obtained solution and reacted under stirring to thereby partially butyl-esterified the acid anhydride. Thus, a partially butyl-esterified styrene-maleic acid copolymer (Bu-SMA) can be obtained. The Bu-SMA thus obtained can be conjugated to an agonist or its biological equivalent by reacting them in a 0.3 M solution of sodium hydrogencarbonate (pH 8.5) so as to form an amide bond between the acid anhydride in Bu-SMA and an amino group in the agonist or its biological equivalent. The bond number of Bu-SMA to MIP-1α or its biological equivalent may be at least 1, preferably from 3 to 10 and still preferably from 6 to 8.

In the case of modifying an amino group in a peptide chain of MIP-1α or its biological equivalent by using PEG as the amphiphilic polymer, it is preferable to introduce a functional group capable of reacting with an amino group (for example, a carboxyl group) into the terminus of PEG. To conjugate the functional group to the amino group in the peptide of MIP-1α or its biological equivalent, it is preferable to convert the functional group into a reactive group. To convert a carboxyl group into a reactive group, for example, it is preferable to employ the active ester method, the mixed acid anhydride method, etc.

In the active ester method, more specifically speaking, use can be made of phenyl esters such as p-nitrophenyl ester and pentafluorophenyl ester, dicarboxylic acid imide esters such as N-hydroxyphthalimide ester and N-hydroxysuccinimide ester, and hydroxyl active esters such as N-hydroxypiperidine ester. These active esters can be prepared in accordance with a method commonly employed in the art. For example, a carboxyl group in a PEG derivative is reacted with an alcohol corresponding to such an active ester at from −20° C. to room temperature for 1 to 24 hours with the use of a condensing agent such as dicyclohexylcarbodiimide or 1-ethyl-3-(3-dimethylaminopropyl)carbodiimide. Alternatively, a carboxyl group in a PEG derivative is reacted with a halide corresponding to such an active ester at from 0° C. to 80° C. for 1 to 72 hours in the presence of a base such as triethylamine. In the mixed acid anhydride method, a PEG derivative is reacted with isobutyl chloroformate, ethyl chloroformate, isovaleryl chloride, etc. at from −20° C. to 0° C. for 1 to 30 minutes in the presence of a base such as N-methylmorpholine or N-ethylpiperidine.

A PEG derivative may be directly introduced into a peptide chain of MIP-1α or its biological equivalent. Alternatively, it is possible to introduce the PEG derivative via a linker arm. For example, a short amino acid sequence having lysine is introduced into the target peptide chain. Then, an amino group in the lysine is modified with the PEG derivative. In the modification reaction, it is preferred to employ the PEG derivative in an amount from 10 to 30 times by mol as much as the amino group number contained in the peptide chain to be modified.

In the case of modifying a carboxyl group in a peptide chain of MIP-1α or its biological equivalent with the use of PEG as the amphiphilic polymer, it is preferable to introduce a functional group capable of reacting with the carboxyl group (for example, an amino group) into the terminus of PEG.

It is expected that the thus obtained MIP-1α or its biological equivalent having been chemically modified with the amphiphilic polymer would accumulate selectively in a target diseased site such as solid tumor due to the so-called EPR effect.

MIP-1α or a biological equivalent thereof according to the present invention is provided as an immunopotentiating agent. That is to say, it is provided as a preventive or a remedy for the onset of an inflammatory disease, an organ injury or cancer in which MIP-1α directly or indirectly participates. Although it is employed preferably as an injection, it may be used in another dosage form such as a suppository or a nasal preparation. Moreover, it can be used together with an anticancer agent commonly employed.

It is preferable that MIP-1α or a biological equivalent thereof according to the present invention is administered in the state where inflammation has been induced in a cancer site and thus the possibility of immune response induction has been elevated. Namely, it is preferable that MIP-1α or a biological equivalent thereof is administered at the point that an inflammation reaction has been sufficiently induced in a cancer site by, for example, radiation irradiation, administration of an adjuvant, freezing and thawing the diseased part or ultrasonic irradiation.

It is known that the radiation therapy for cancer can not only damage cancer cells but also cause an inflammation reaction in the radiation-irradiated part so as to induce an immune response in cancer other than the irradiated site (the abscopal effect). It has been found out that when used together with the radiation therapy commonly employed, MIP-1α or a biological equivalent thereof according to the present invention can potentiate the abscopal effect caused by the radiation irradiation and further improve the clinical effect.

MIP-1α or a biological equivalent thereof according to the invention can be used together with an adjuvant commonly employed so as to potentiate the immune response induced by the adjuvant and improve the clinical effect. As the adjuvant for the combined use, it is possible to employ commonly employed adjuvants such as krestin, picibanil, lentinan, bestatin or *P. acnes*.

When used together with the freezing and thawing therapy for inducing the necrosis of a cancer tissue, MIP-1α or a biological equivalent thereof according to the invention can induce the necrosis and regression of the cancer tissue. Furthermore, MIP-1α or a biological equivalent thereof according to the invention can be used together with a commonly employed anticancer agent or the radiation irradiation therapy, the freezing and thawing therapy or the ultrasonic irradiation therapy for inhibiting tumor metastasis.

MIP-1α or a biological equivalent thereof according to the invention is also applicable to treatments for immunologic diseases such as pollinosis. It is possible to use either MIP-1α or a biological equivalent alone or a combination thereof with a commonly employed antiallergic agent, an antihistaminic agent or the like.

In the immunopotentiating agent according to the present invention, it is preferable to parenterally administer MIP-1α or its biological equivalent (i.e., a protein) employed as the active ingredient. For example, it is preferable to administer the agent as an injection or the like in the form of an aseptic solution or suspension in water or a pharmaceutically acceptable liquid. An aseptic composition for injection can be prepared in accordance with formulation means commonly employed, for example, dissolving or suspending the active ingredient in a vehicle such as injection water or a natural vegetable oil. As an aqueous liquid for injection, use can be made of, for example, physiological saline, an isotonic solution containing glucose and other auxiliaries (for example, D-sorbitol, D-mannitol or sodium chloride), etc. It is also possible to further employ an appropriate dissolution aid such as an alcohol (for example, ethanol), a polyalcohol (for example, propylene glycol or polyethylene glycol), a nonionic surfactant (for example, Polysorbate 80™ or HCO-50) and so on. As an oily liquid, use can be made of, for example, sesame oil, palm oil or soybean oil. As a dissolution aid, it is also possible to further blend benzyl benzoate, benzyl alcohol, etc. Moreover, use may be made of a buffer agent (for example, a phosphate buffer solution or a sodium acetate buffer solution), a soothing agent (for example, benzalkonium chloride or procaine hydrochloride), a stabilizer (for example, human serum albumin or polyethylene glycol), a preserving agent (for example, benzyl alcohol or phenol), an antioxidant and so on.

MIP-1α or its biological equivalent having Bu-SMA conjugated thereto which is obtained in the present invention can be used as a water-soluble or oily injection. A water-soluble injection is employed mainly in intravenous administration. An oily injection, which is prepared by uniformly dispersing MIP-1α or its biological equivalent having Bu-SMA conjugated thereto in an oily agent such as Lipiodol, is administered to a target diseased site such as solid tumor via, for example, a catheter fixed in the upstream of the tumor feeding artery. The present inventors have found out that an agonist or its biological equivalent having Bu-SMA conjugated thereto binds to albumin in the blood and thus behaves as a high-molecular weight compound and that the Bu-SMA-conjugated compound is soluble in an oily agent. Accordingly, it is expected that, when topically injected into the desired artery, the Bu-SMA-conjugated MIP-1α or its biological equivalent in the form of an oily preparation would accumulate selectively in the target diseased site such as a solid tumor due to the so-called EPR effect.

The preparation thus obtained can be administered to humans or other mammals. Although the dose of the active ingredient according to the present invention varies depending on the disease to be treated, the subject of administration, the administration route and so on, the single dose of the active ingredient in parenteral administration to an adult (assumed as weighing 60 kg) ranges from, for example, about 0.01 to about 20 mg, preferably from about 0.1 to about 10 mg. To other animals, it may be administered in a dose calculated in terms of body weight with the use of 60 kg as the basis. In addition to an injection, the immunopotentiating agent according to the present invention is usable as, for example, a suppository or a nasal preparation.

Referential Example 1

Method of Producing MIP-1α

Human MIP-1α gene was obtained by the PCR method. Then this human MIP-1α gene was integrated into an expression shuttle vector pNCMO2 and amplified in *Escherichia coli*. The human MIP-1α gene expression vector was transferred into *Brevibacillus chonshinensis* (*B. chonshinensis*) HPD31S5. This *B. chonshinensis* having the human MIP-1α gene transferred thereinto was cultured and the supernatant was collected. To this culture supernatant was added ammonium sulfate to achieve 40% saturation. After forming a precipitate, the supernatant was separated by centrifuging and ammonium sulfate was further added thereto to give 60% saturation. After forming a precipitate, the precipitate was collected by centrifuging. Then this precipitate was dissolved in a tris hydrochloride buffer (pH 8.0) and the obtained solution was fractionated by anion exchange chromatography (Q Sepharose; manufactured by Amersham). From the obtained fractions, those containing MIP-1α were combined and dissolved by adding ammonium sulfate (final concentration: 1.5 M). The obtained solution was fractionated by hydrophobic chromatography (RESOURCE PHE; manufactured by Amersham). From the obtained fractions, those containing MIP-1α (unadsorbed fractions) were combined and subjected to ammonium sulfate precipitation by adding ammonium sulfate (final concentration: 60% saturation). The precipitate was dissolved in a tris hydrochloride buffer (pH 8.0). The solution was fractionated again by anion exchange chromatography (RESOURCE Q: manufactured by Amersham). From the obtained fractions, those containing MIP-1α were combined and dialyzed against 20 mM $NH_4HCO_3$ (pH 8.5) to thereby remove the tris salt. By centrifuging the precipitate obtained by this treatment, purified human MIP-1α was obtained. After freeze-drying, the product was dissolved in PBS and used in the following experiments.

Referential Example 2

Method of Producing eMIP

Expression and Purification cDNA of eMIP was prepared by site-specific mutation with Quik Change Kit (manufactured by Stratagene) with the use of human MIP-1α cDNA as a template. Namely, 1 μl of Pfu-turbo (2.5 U/μl) was added to 50 μl of a reaction system containing 125 ng of mutation primers RQ1:5'-CCAGC-GAAGCCGGCAGGTCTGTGCTGACCCAG-3' (SEQ ID NO:1) and RQ2:5'-CTGGGGTCAGCACAGACCTGCCG-GCTTCGCTTGG-3' (SEQ ID NO:2), 10 ng of the template plasmid DNA and 50 μM of dNTP. After denaturation at 95° C. for 30 seconds, the reaction was performed for 12 cycles with each cycle consisting of 30 seconds at 95° C., 1 minute at 55° C. and 7 minutes at 68° C. Subsequently, 1 μl of a restriction enzyme DpnI was added to the reaction system and the reaction was carried out at 37° C. for 1 hour. Thus, the template DNA was cut off and the mutated plasmid alone was recovered. After confirming that the mutation site had been correctly substituted by DNA sequence analysis, it was inserted into a fission yeast expression plasmid vector pTL2M5. By using this plasmid, *Schizosaccharomyces pombe* was transformed to obtain an eMIP-expressing strain.

Next, this strain was cultured in 16 L of the YPD medium (0.5% yeast extract, 2% peptone, 2% glucose) containing 100 μg/ml of an antibiotic G418 at 30° C. for 48 hours to thereby allow expression and secretion in the medium. The supernatant of the culture medium was subjected to sterile filtration through a 0.45 μm filter to give a starting material for purification.

The recombinant eMIP protein was purified by using the AKTA-prime system (manufactured by Amersham Bioscience). Namely, a formic acid buffer solution (0.5 M formic acid (pH 4.0)) was added to the supernatant of the culture medium and then Tween 20 was further added to give a final concentration of 0.01%. The obtained sample was supplied into cation exchange columns SP-XL (six 5 ml columns connected together; manufactured by Amersham Bioscience) at a rate of 2 ml/min. After adsorption, gradient elution was conducted with the use of a formic acid buffer solution (pH 7.0) containing 1M of sodium chloride. After confirming by 10 to 20% SDS-polyacrylamide gel electrophoresis (SDS-PAGE), a peak fraction was collected. Then, it was dialyzed against a 10 mM phosphate buffer solution (pH 7.0) and supplied into heparin affinity columns (four 5 ml columns connected together; manufactured by Amersham Bioscience) at a rate of 2 ml/min. After adsorption, gradient elution was conducted with the use of a phosphate buffer solution (pH 7.0) containing 1 M of sodium chloride. After confirming by 10 to 20% SDS-PAGE, a peak fraction was collected. The yield was 175 mg per 16 L of the culture. After dialyzing against a physiological phosphate buffer solution (PBS(−) (pH 7.4)), the product was used in animal experiments.

Referential Example 3

Method of Producing Bu-SMA-Conjugated eMIP

Figure 7:
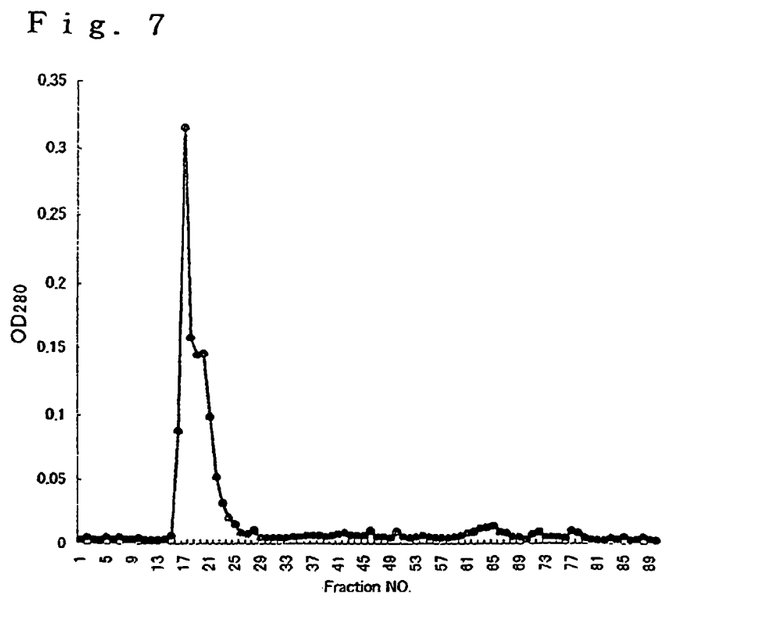
FIG. 7 shows the optical densities at 280 nm of the individual Bu-SMA-BB10010 fractions.

The eMIP obtained in Referential Example 2 was dissolved in a 0.8 M sodium hydrogencarbonate buffer solution (pH 8.5) to give a concentration of 2 mg/ml. Per ml of this solution, 2.6 mg of Bu-SMA (molar ratio of Bu-SMA:eMIP=10:1) dissolved in diethylformamide was gradually added to and the resultant mixture was reacted at 27° C. overnight. After the completion of the reaction, the reaction mixture was subjected to gel filtration chromatography (packing agent: Bio-Gel P60, manufactured by Bio-Rad Laboratories, mobile phase: 20 mM ammonium hydrogencarbonate solution (pH 8.5), column size: 1.6×83 cm) to thereby purify the Bu-SMA-conjugated eMIP. The eluate was collected into 90 test tubes in 2 m portions (FIG. 7). Based on the optical densities at 280 nm, the fractions eluted in test tubes No. 16 to No. 18 (6 ml in total) were freeze-dried to give the Bu-SMA-conjugated eMIP (hereinafter referred to as "Bu-SMA-eMIP") as a white powder.

Figure 8:
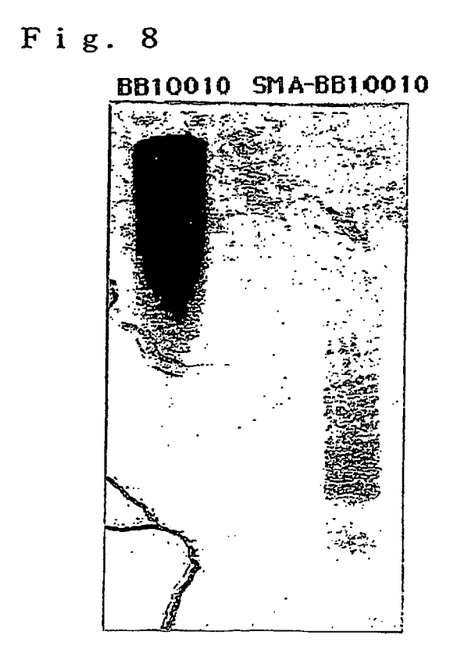
FIG. 8 shows native-PAGE patterns of Bu-SMA-BB10010 and BB10010 that is the starting material thereof.

FIG. 8 shows native-PAGE (unmodified 10 to 20% gradient polyacrylamide gel electrophoresis) patterns of the thus obtained Bu-SMA-eMIP and eMIP employed as the starting material thereof. These two substances showed obviously different migration distances. This is seemingly because Bu-SMA-eMIP was more easily electrophoresed in the anode side, since an amino group in lysine of eMIP was modified by SMA and the positive surface charge was thus lowered. Based on the difference in migration distance between these substances and quantification results, which were obtained by reacting Bu-SMA-eMIP in the fractions No. 16 to No. 18, unreacted Bu-SMA and amino groups in eMIP with a fluorescent reagent Fluorescamine (0.3 mg/ml in acetone) and measuring the fluorescences with a spectrofluorometer at an excitation wavelength of 390 nm and a fluorescence wavelength of 475 nm, it was estimated that 2 to 3 SMA units had been conjugated per molecule.

Example 1

Combination of eMIP with Radiation Therapy

1) Test Method

By using female C57BL/6 mice aged 7 weeks and Lewis lung carcinoma (3LL), the effect of the combination of eMIP with electron beam irradiation therapy on the solid tumor was evaluated.

$4 \times 10^5$ 3LL cells were subcutaneously transplanted into the flank position of each animal. When the solid tumor size (diameter) attained about 1 cm (after 19 days), the animals were re-divided into groups depending on the solid tumor size. Then the cancer tissue was irradiated with an electron beam. On the next day, eMIP was administered into the tail vein. Subsequently, eMIP administration was continued once a week, 4 times in total. As a control, 5Fu was intraperitoneally administered in a dose of 25 mg/kg from the next day of the electron beam irradiation twice a week.

Tumor volume was calculated in accordance with the following formula reported by Janik et al.

$$(\text{Tumor volume}) = (\text{Major tumor diameter}) \times (\text{Minor tumor diameter})^2 \times 0.5236$$

2) Test Results

Concerning the proliferation of the 3LL lung cancer cells, the electron beam irradiation exerted a dose-depending inhibition effect (2, 6 and 10 Gy) on the proliferation of the solid tumor. Although the administration of eMIP alone (50 μg/mouse) showed a tendency toward the inhibition, no significant effect was observed. When the electron beam irradiation was combined with the administration of eMIP (50 μg/mouse), eMIP significantly potentiated the antitumor effect of the electron beam at 6 and 10 Gy (FIGS. 1A and B).

Figure 1:
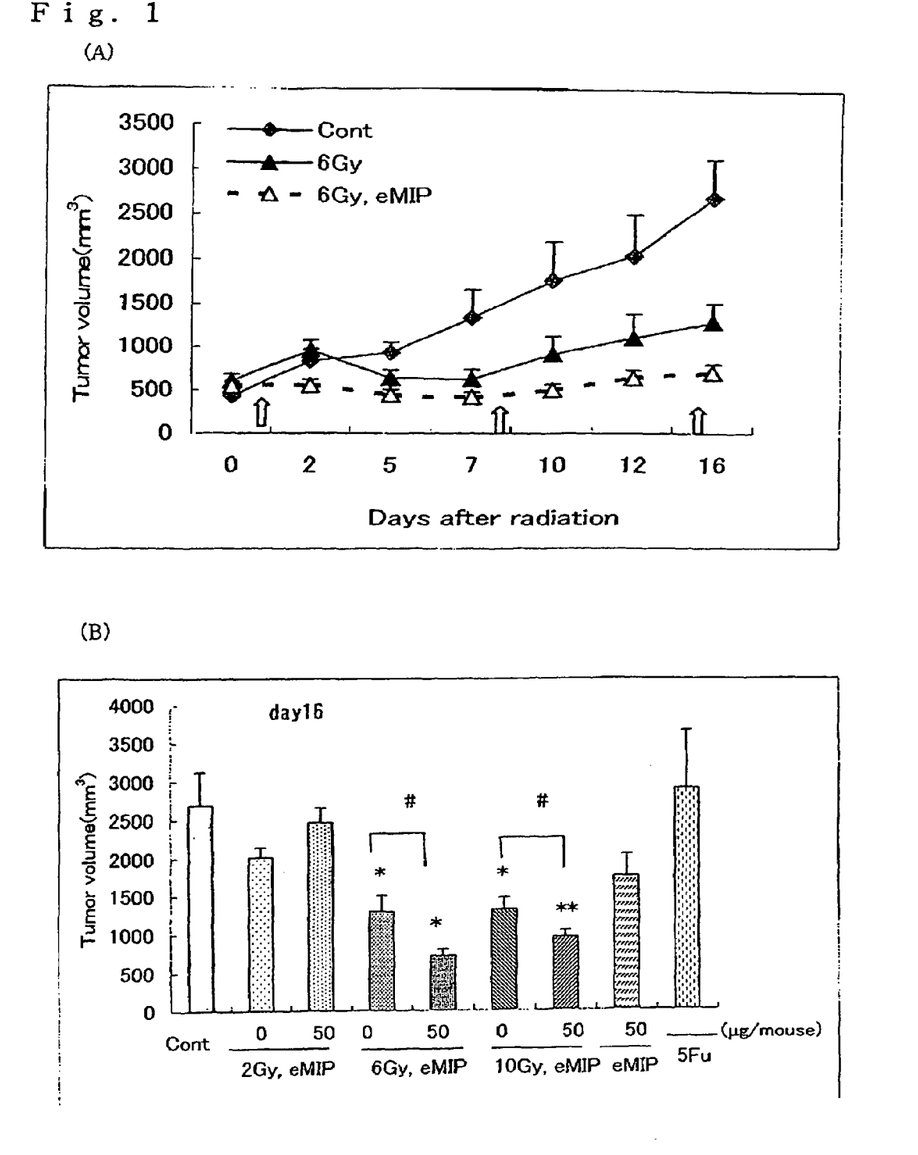
FIG. 1 shows the effects of the combined use of eMIP with radiation therapy on 3LL cancer-carrying mice.

FIG. 1(A) shows the effects of the combined use of eMIP with the electron beam (6 Gy). When the solid tumor size attained about 1 cm, the 3LL-carrying mice (n=5) were irradiated with the electron beam. On the next day, eMIP was intravenously administered to the animals followed by intravenous administration once a week. In this drawing, each ⇑shows an eMIP administration day.

FIG. 1(B) shows the antitumor effects of eMIP on the 16th day after the electron beam irradiation (n=5). In this drawing, "*", "**" and "#" respectively show $p<0.05$, $p<0.01$ (ANOVA) and $p<0.05$ (t-test).

Example 2

Effect of Potentiating Abscopal Effect

1) Test method

By using female C57BL/6 mice aged 7 weeks and Lewis lung carcinoma (3LL), the effects of the combination of eMIP with electron beam irradiation therapy on the solid tumors transplanted into the right and left flanks regions were compared and evaluated.

$4 \times 10^5$ 3LL cells were subcutaneously transplanted into the right flank position of each animal (the primary tumor). At the same time, $2 \times 10^5$ 3LL cells were subcutaneously transplanted into the left flank position of each animal (the secondary tumor). When the solid tumor size (diameter) in the right flank position attained about 1 cm (on the 19th day), the animals were re-divided into groups depending on the solid tumor size. Then the tumor in the right flank position was irradiated with an electron beam with the use of a linear accelerator (electron beam irradiation dose: 6 Gy). On the next day of the electron beam irradiation, eMIP was intravenously administered. Subsequently, eMIP was administered at 8 and 15 days after irradiation, i.e., three times in total. The diameters of the tumors in the right and left flanks were measured and the antitumor effects were evaluated based on the tumor volume.

Tumor volume was calculated in accordance with the following formula reported by Janik et al.

$$(\text{Tumor volume}) = (\text{Major tumor diameter}) \times (\text{Minor tumor diameter})^2 \times 0.5236$$

2) Test Results

Figure 2:
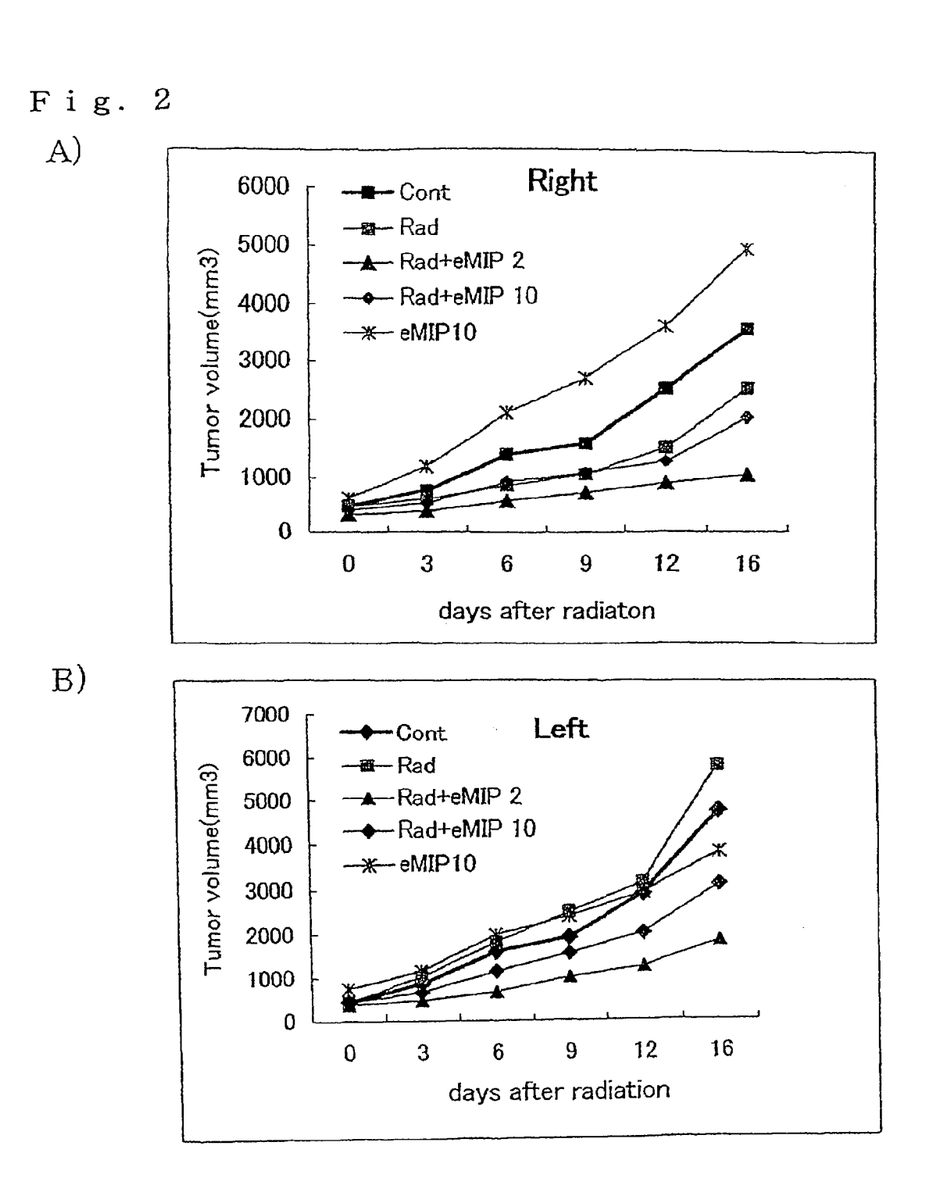
FIG. 2 shows changes in the potentiation of the abscopal effect by eMIP observed within 16 days following electron beam irradiation.
Figure 3:
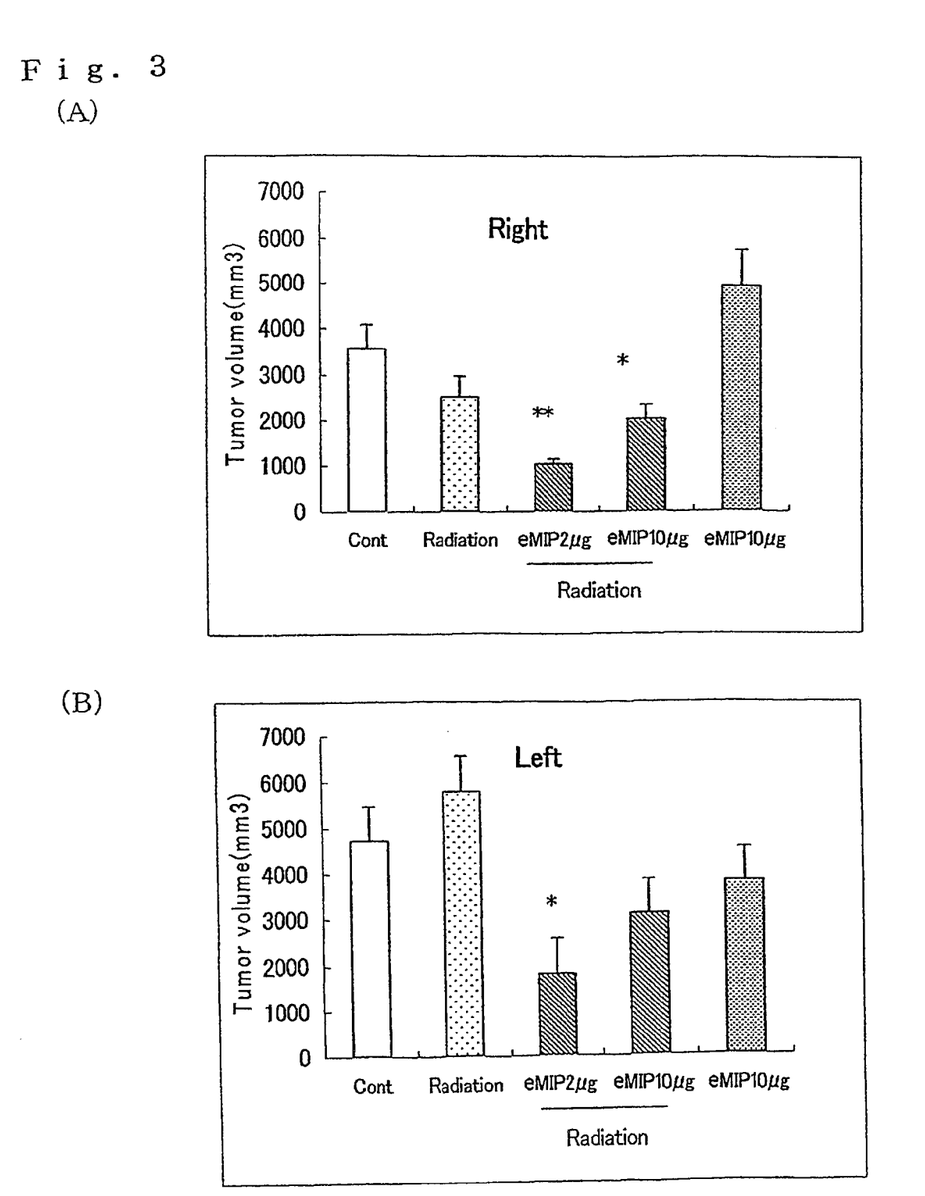
FIG. 3 shows the potentiation of the abscopal effect by eMIP observed on the 17th day after electron beam irradiation.

FIG. 2 shows changes in the tumor volumes in the right and left flanks within 16 days following electron beam irradiation, while FIG. 3 shows the results on the 17th day. In each of FIGS. 2 and 3, (A) shows changes in the tumors in the right flank position caused by the electron beam irradiation, while (B) shows changes in the tumors in the left flank position caused by the electron beam irradiation.

Figure 4:
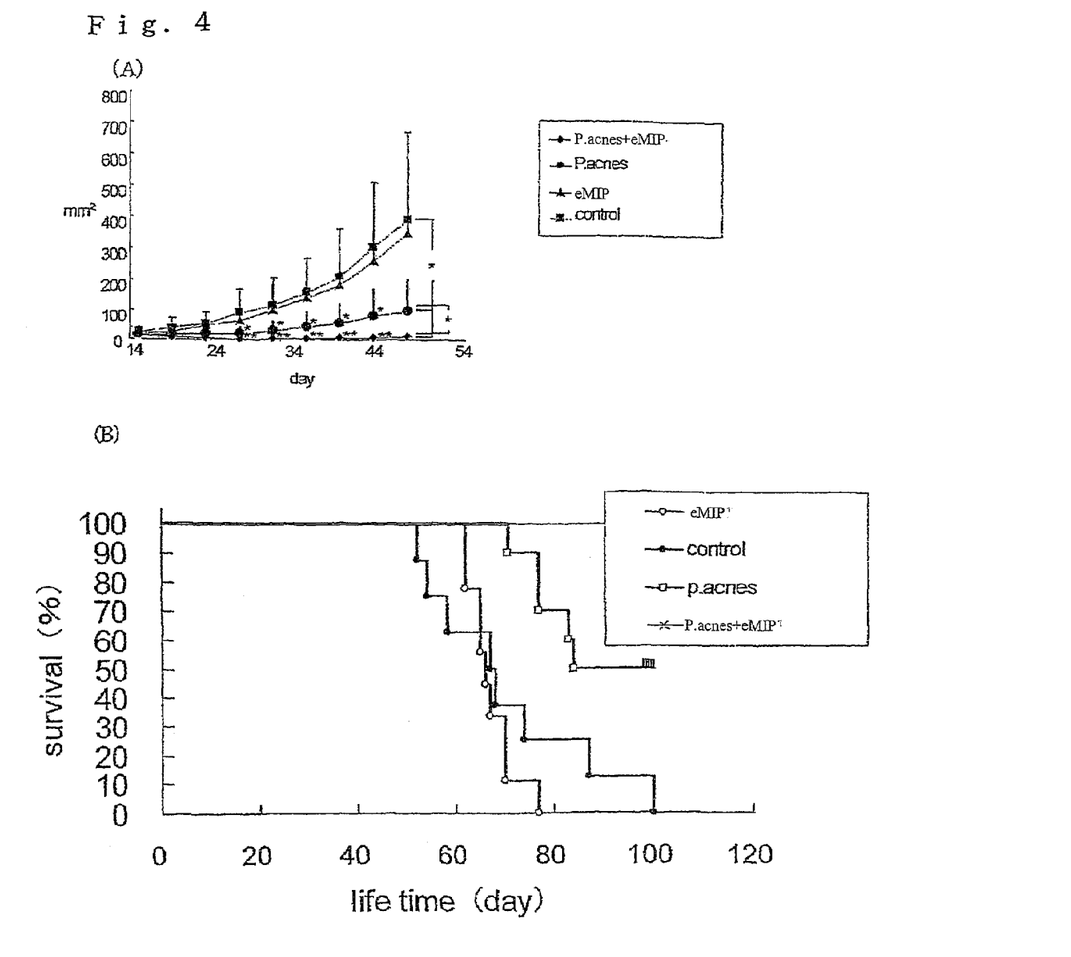
FIG. 4 shows the effects of the combined use of an adjuvant (*P. acnes*) treatment with eMIP on 3LL tumor.

As -■- in FIG. 2(A) shows, the proliferation of the tumors in the right flank position was inhibited by irradiating the tumors in the right flank position with the electron beam. As -■- in FIG. 2(B) shows, on the other hand, the proliferation of the tumors in the left flank position was not inhibited thereby. It is interesting that owing to the combined use of eMIP, the proliferation of the tumors in the left flank position not irradiated with the electron beam was significantly inhibited (60% or above) at a dose of 2 μg/mouse. In the tumors in the right flank position having been irradiated with the electron beam, the antitumor effect of the electron beam was significantly potentiated in a dose of 2 μg/mouse or 10 μg/mouse (FIG. 3). In FIG. 4, "*" and "**" respectively show $p<0.05$ and $p<0.01$ (ANOVA) from the control group (Cont).

These results indicate that eMIP potentiates the abscopal effect. That is, it is clarified that eMIP not only potentiates the inflammation or immune response at the tumor site having been subjected to the radiation irradiation but also activates the systemic antitumor immune responses.

Actually, the 3LL cancer-carrying mice having been subjected to the radiation irradiation and eMIP administration showed an increase in γ-interferon producing cells in the spleen and the increase level was significantly higher than the control mice and the mice subjected to the radiation irradiation alone.

Based on these results, it can be concluded that eMIP provides a therapeutic method in electron beam irradiation therapy that is efficacious not only on the irradiated tumor but also on a tumor at a non-irradiated site such as a metastatic focus.

Example 3

Effect of the Combination of eMIP with Adjuvant

1) Test Method

By using female C57BL/6 mice aged 8 to 10 weeks and Lewis lung carcinoma (3LL), the effects of the combination of the adjuvant therapy with eMIP on the solid tumors were evaluated.

On the 1st, 8th, 15th and 22nd days following the subcutaneous transplantation of $2 \times 10^5$ 3LL cells, 20 μg of dead *Propionibacterium acnes* (11828; American Type Culture Collection, Manassas, Va.) cells suspended in 40 μl of PBS were subcutaneously injected into the same site. On the 2nd, 9th, 16th and 23rd days, 20 μg of eMIP dissolved in 100 μl of PBS was administered via the tail vein.

Tumor proliferation was evaluated by measuring the major diameter.

2) Test Results

Concerning the proliferation of the 3LL cells, the adjuvant (*P. acnes*) alone showed a significant activity of inhibiting the proliferation. By administering eMIP once a week in addition to the adjuvant, the tumor proliferation was almost completely inhibited. No significant inhibition effect was observed by administering eMIP alone (FIG. 4A). Concerning the survival rate of the mice, all animals died during the 70th to 100th days in the control group and the group with the administration of eMIP alone. In contrast, 50% of the mice survived for 100 days or longer in the group with the administration of the adjuvant alone and 100% of the mice survived in the group with the administration of eMIP once a week in addition to the adjuvant (FIG. 4B). FIG. 4A shows the results obtained by subcutaneously injecting 3LL, subcutaneously injecting dead *P. acnes* cells on the 1st, 8th, 15 and 22 days and further administering eMIP on the 2nd, 9th, 16th and 23rd days via the tail vein. Tumor proliferation was evaluated by measuring the major diameter. "*" shows $p<0.05$. FIG. 4B shows the survival rates of the mice in the same test wherein x stands for eMIP and *P. acnes*; □ stands for *P. acnes* alone; ○ stands for MIP-1α alone; and ● stands for the untreated case.

The following table shows the statistical significant differences of the numerical values in FIG. 4B.

|  | Logrank test | | | Generalized Wilcoxon test | | |
|---|---|---|---|---|---|---|
|  | $X^2$ value | p value | SD | $Z^2$ value | p value | SD |
| eMIP vs. control | 5.0443E−01 | 4.7756E−01 | No | 2.0936E−02 | 8.8495E−01 | No |
| eMIP vs. *P. acnes* | 1.3305E+01 | 2.6463E−04 | p < 0.0005 | 1.2626E+01 | 3.8056E−04 | p < 0.0005 |
| eMIP vs. *P. acnes* eMIP | 1.5059E+01 | 1.0418E−04 | p < 0.0005 | 1.3432E+01 | 2.4742E−04 | p < 0.0005 |
| Control vs. *P. acnes* | 7.3482E+00 | 6.7131E−03 | p < 0.01 | 6.7866E+00 | 9.1848E−03 | p < 0.01 |

-continued

| | Logrank test | | | Generalized Wilcoxon test | | |
|---|---|---|---|---|---|---|
| | $\hat{X}2$ value | p value | SD | $\hat{Z}2$ value | p value | SD |
| Control vs. P. acnes eMIP | 1.5730E+01 | 7.3062E−05 | p < 0.0001 | 1.2886E+01 | 3.3114E−04 | p < 0.0005 |
| P. acnes vs. P. acnes eMIP | 4.9617E+00 | 2.5915E−02 | p < 0.05 | 5.0662E+00 | 2.4396E−02 | p < 0.05 |

SD: significant difference.

Example 4

Tumor Metastasis Inhibition Effect of eMIP

1) Test Method

By using a lung metastasis system of Lewis lung carcinoma (3LL), the tumor metastasis inhibition effect of eMIP was evaluated. Female C57BL/6 mice aged 7 weeks were employed. $10^6$ 3LL cells were injected into each animal via the tail vein. After 25 days, the lungs were taken out, weighed and fixed with Bouin' solution. Then, cancer tissues metastasized into the lungs were counted under a stereoscopic microscope. 30 minutes after the 3LL transplantation, eMIP was injected as the first administration followed by continuous administration once a week for 4 weeks. In the system wherein the administration was initiated 7 days after the 3LL transplantation, the effect of eMIP was examined. 5Fu employed as a control was administered twice a week.

2) Test Results

Figure 5:
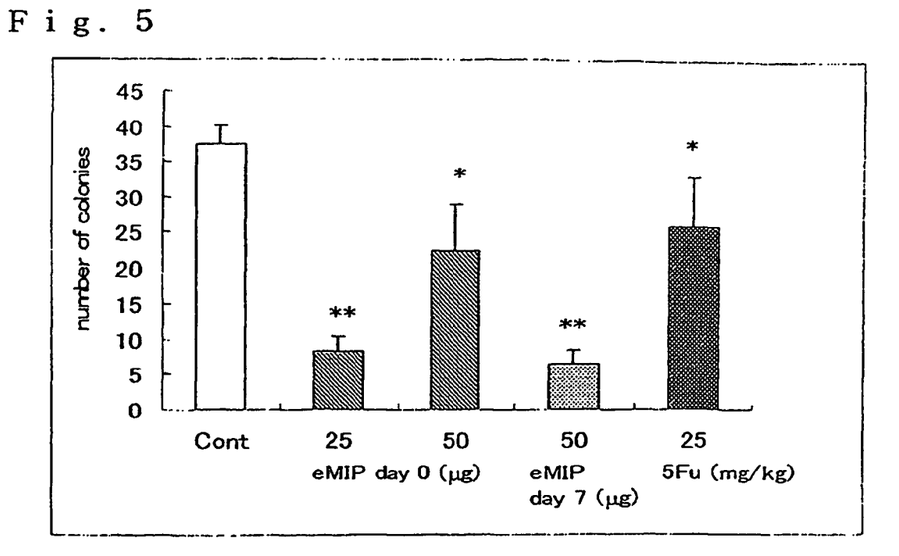
FIG. 5 shows the inhibition effects of eMIP on the lung metastasis of 3LL tumor.
Figure 6:
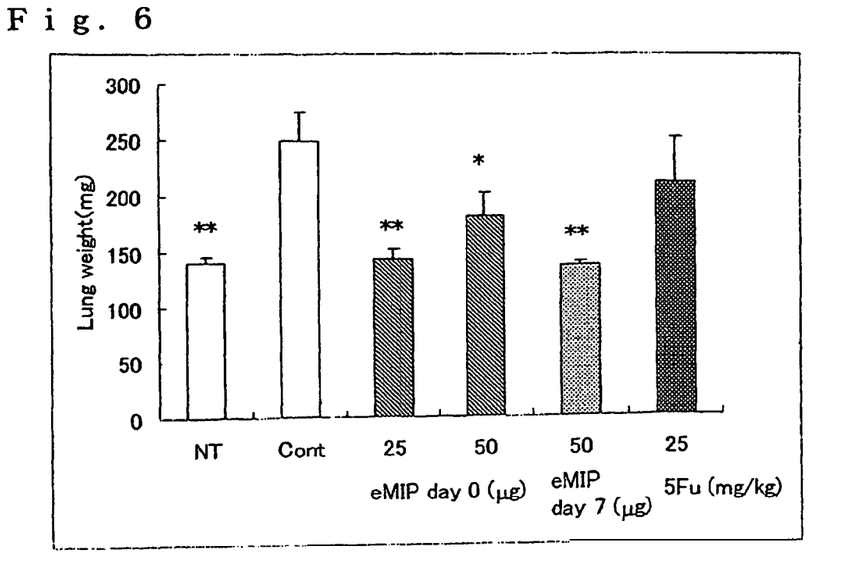
FIG. 6 shows the lung weights of mice carrying 3LL having been intravenously transplanted.

FIG. 5 shows the results. eMIP significantly inhibited the metastasis into the lungs, while the administration of 5Fu (25 mg/mouse) showed an inhibition rate of 78%. When the administration was initiated 7 days after the 3LL transplantation, eMIP also inhibited the metastasis of 3LL into the lungs. Similarly, an increase in the lung weight caused by the metastasis of 3LL into the lungs was also regulated with correlating to the effect of inhibiting the metastasis into the lungs (FIG. 6). In FIG. 5, day 0 shows the data obtained in the case where the eMIP administration was initiated 30 minutes after the 3LL transplantation; and day 7 shows the data obtained in the case where the eMIP administration was initiated 7 days after the 3LL transplantation. In FIG. 5, significant differences from the control group are as follows: *: p<0.05, **: p<0.01 (ANOVA). n=10 (the control group), n=7 (the eMIP and 5 Fu administration groups). In FIG. 6, significant differences from the control group are as follows: *: p<0.05; **: p<0.01 (ANOVA). n=10 (the control group), n=7 (the eMIP and 5 Fu administration groups).

INDUSTRIAL APPLICABILITY

The present invention provides a remedy, which is efficacious in further developing the currently available immunotherapy for cancer and inducing immunity against cancer, as well as a remedy for treating an immunologic disease such as pollinosis.

In the present invention, MIP-1α or its functional derivative is administered after topically inducing inflammation at a cancer site. As a result, remarkable effects of inhibiting cancer proliferation and elevating the survival rate are established. Furthermore, the administration of MIP-1α or its functional derivative exerts effects of remarkably inhibiting tumor metastasis and ameliorating immunologic diseases such as pollinosis.

According to the present invention, therefore, it is indicated that MIP-1α or its functional derivative obviously accelerates an immune response and drastically potentiates the efficacy of immunotherapy. Therefore, it can be said that the potential usefulness of MIP-1α or its functional derivative is thus demonstrated.

The invention claimed is:

1. A method for potentiating the abscopal effect in a subject undergoing radiation therapy for cancer, comprising:
   administering to said subject an effective amount of eMIP.

2. A method for treating cancer in a subject, comprising the steps of:
   exposing said cancer to radiation; and
   administering to said subject an effective amount of eMIP in an amount to potentiate an abscopal effect caused by said step of exposing said cancer to radiation.

3. The method according to claim 1 or 2, wherein said effective amount is 0.01 to about 20 mg per 60 kg weight of said subject.

4. The method according to claim 3, wherein said effective amount is 0.1 to about 10 mg per 60 kg weight of said subject.

5. The method according to claim 1 or 2, wherein said effective amount of eMIP is administered by injection, suppository or nasal preparation.

6. The method according to claim 1 or 2, wherein said effective amount of eMIP is administered within a medicine that is administered additionally with a medicine containing an adjuvant as the active ingredient, wherein said medicines are simultaneously or sequentially administered.

7. The method according to claim 1, wherein said radiation therapy is with an electron beam.

8. The method according to claim 2, wherein said radiation is radiation therapy with an electron beam.

9. The method according to claim 1, wherein said subject is administered eMIP after undergoing radiation therapy.

10. A method for treating a cancer subject undergoing therapy for said cancer, comprising:
    administering to said subject an effective amount of eMIP at a time when inflammation has been caused in said patient by said therapy.

11. The method according to claim 10, wherein the therapy that caused the inflammation is selected from the group consisting of radiation irradiation, administration of an adjuvant, freezing and thawing the diseased tissue and ultrasonic irradiation.

12. The method according to claim 10, wherein said effective amount of eMIP is administered within a medicine that is administered additionally with a medicine containing an adjuvant as the active ingredient, wherein said medicines are simultaneously or sequentially administered.

13. The method according to claim 6 wherein said adjuvant is selected from the group consisting of krestin, picibanil, lentinan, bestatin and *P. acnes*.

14. A method for potentiating the abscopal effect in a subject undergoing radiation therapy for cancer, comprising:
    administering to said subject an effective amount of eMIP chemically modified with an ampliphilic polymer.

15. A method for treating cancer in a subject, comprising the steps of:
    exposing said cancer to radiation; and
    administering to said subject an effective amount of eMIP chemically modified with an amphiphilic polymer in an amount to potentiate an abscopal effect caused by said step of exposing said cancer to radiation.

16. The method according to claim 14 or 15, wherein said effective amount is 0.01 to about 20 mg per 60 kg weight of said subject.

17. The method according to claim 16, wherein said effective amount is 0.1 to about 10 mg per 60 kg weight of said subject.

18. The method according to claim 14 or 15, wherein said effective amount of eMIP chemically modified with an amphiphilic polymer is administered by injection, suppository or nasal preparation.

19. The method according to claim 14 or 15, wherein said effective amount of eMIP chemically modified with an amphiphilic polymer is administered within a medicine that is administered additionally with a medicine containing an adjuvant as the active ingredient, wherein said medicines are simultaneously or sequentially administered.

20. A method for potentiating the abscopal effect in a subject undergoing radiation therapy for cancer, comprising:
    administering to said subject an effective amount of eMIP chemically modified with a partially alkyl-esterified styrene/maleic acid copolymer or a polyethylene glycol derivative.

21. A method for treating cancer in a subject, comprising the steps of:
    exposing said cancer to radiation; and
    administering to said subject an effective amount of eMIP chemically modified with a partially alkyl-esterified styrene/maleic acid copolymer or a polyethylene glycol derivative in an amount to potentiate an abscopal effect caused by said step of exposing said cancer to radiation.

22. The method according to claim 20 or 21, wherein said effective amount is 0.01 to about 20 mg per 60 kg weight of said subject.

23. The method according to claim 22, wherein said effective amount is 0.1 to about 10 mg per 60 kg weight of said subject.

24. The method according to claim 20 or 21, wherein said effective amount of eMIP chemically modified with a partially alkyl-esterified styrene/maleic acid copolymer or a polyethylene glycol derivative is administered by injection, suppository or nasal preparation.

25. The method according to claim 20 or 21, wherein said effective amount of eMIP chemically modified with a partially alkyl-esterified styrene/maleic acid copolymer or a polyethylene glycol derivative is administered within a medicine that is administered additionally with a medicine containing an adjuvant as the active ingredient, wherein said medicines are simultaneously or sequentially administered.

26. A method for treating a cancer subject undergoing therapy for said cancer, comprising:
    administering to said subject an effective amount of eMIP chemically modified with an amphiphilic polymer at a time when inflammation has been caused in said patient by said therapy.

27. The method according to claim 26, wherein the therapy that caused the inflammation is selected from the group consisting of radiation irradiation, administration of an adjuvant, freezing and thawing the diseased tissue and ultrasonic irradiation.

28. The method according to claim 26, wherein said effective amount of eMIP chemically modified with an amphiphilic polymer is administered within a medicine that is administered additionally with a medicine containing an adjuvant as the active ingredient, wherein said medicines are simultaneously or sequentially administered.

29. A method for treating a cancer subject undergoing therapy for said cancer, comprising:
    administering to said subject an effective amount of eMIP chemically modified with a partially alkyl-esterified styrene/maleic acid copolymer or a polyethylene glycol derivative at a time when inflammation has been caused in said patient by said therapy.

30. The method according to claim 29, wherein the therapy that caused the inflammation is selected from the group consisting of radiation irradiation, administration of an adjuvant, freezing and thawing the diseased tissue and ultrasonic irradiation.

31. The method according to claim 29, wherein said effective amount of eMIP chemically modified with a partially alkyl-esterified styrene/maleic acid copolymer or a polyethylene glycol derivative is administered within a medicine that is administered additionally with a medicine containing an adjuvant as the active ingredient, wherein said medicines are simultaneously or sequentially administered.

32. The method according to claim 19 wherein said adjuvant is selected from the group consisting of krestin, picibanil, lentinan, bestatin and *P. acnes*.

33. The method according to claim 25 wherein said adjuvant is selected from the group consisting of krestin, picibanil, lentinan, bestatin and *P. acnes*.

34. The method according to any one of claims 12, 28 and 31 wherein said adjuvant is selected from the group consisting of krestin, picibanil, lentinan, bestatin and *P. acnes*.

* * * * *

SEQUENCE LISTING

<160> NUMBER OF SEQ ID NOS: 2

<210> SEQ ID NO 1
<211> LENGTH: 32
<212> TYPE: DNA
<213> ORGANISM: Homo sapiens

<400> SEQUENCE: 1
ccagcgaagc cggcaggtct gtgctgaccc ag        32

<210> SEQ ID NO 2
<211> LENGTH: 34
<212> TYPE: DNA
<213> ORGANISM: Homo sapiens

<400> SEQUENCE: 2
ctggggtcag cacagacctg ccggcttcgc ttgg        34